United States Patent [19]

Neckers et al.

[11] Patent Number: 5,639,802
[45] Date of Patent: Jun. 17, 1997

[54] CATIONIC POLYMERIZATION

[75] Inventors: Douglas C. Neckers, Perrysburg; Yubai Bi, Bowling Green, both of Ohio

[73] Assignee: Spectra Group Limited, Inc., Maumee, Ohio

[21] Appl. No.: 156,453

[22] Filed: Nov. 23, 1993

Related U.S. Application Data

[63] Continuation-in-part of Ser. No. 881,048, May 11, 1992, abandoned, and Ser. No. 772,103, Oct. 7, 1991, abandoned, which is a continuation-in-part of Ser. No. 756,611, Sep. 9, 1991, abandoned, which is a continuation-in-part of Ser. No. 702,886, May 20, 1991, abandoned.

[51] Int. Cl.$^6$ .............................. C08L 63/00; C08F 2/50
[52] U.S. Cl. .............................. 522/25; 522/26; 522/27; 522/29; 522/168; 522/170; 522/172; 522/174; 522/178; 522/181
[58] Field of Search ............................... 522/25, 26, 27, 522/29, 168, 170, 172, 174, 178, 181

[56] References Cited

U.S. PATENT DOCUMENTS

| | | | |
|---|---|---|---|
| 1,885,592 | 11/1932 | Coulthard et al. | 549/394 |
| 2,157,351 | 5/1939 | Schneider et al. | 260/328 |
| 2,875,047 | 2/1959 | Oster | 96/35 |
| 3,808,006 | 4/1974 | Smith | 96/88 |
| 4,329,461 | 5/1982 | Khanna et al. | 544/375 |
| 4,343,885 | 8/1982 | Reardon | 430/177 |
| 4,481,136 | 11/1984 | Khanna et al. | 260/112 R |
| 4,492,762 | 1/1985 | Wang et al. | 436/537 |
| 4,552,830 | 11/1985 | Reardon et al. | 430/281 |
| 4,585,862 | 4/1986 | Wang et al. | 544/319 |
| 4,647,675 | 3/1987 | Mayer et al. | 549/394 |
| 4,716,097 | 12/1987 | Weed | 430/327 |

(List continued on next page.)

FOREIGN PATENT DOCUMENTS

| | | | |
|---|---|---|---|
| 0507493 | 3/1992 | European Pat. Off. | C08G 77/385 |
| 0530095 | 8/1992 | European Pat. Off. | C08F 2/50 |
| 59-176641 | 6/1984 | Japan | G01M 3/20 |
| 1058516 | 2/1967 | United Kingdom | A61K 3/00 |
| 1123767 | 8/1968 | United Kingdom . | |
| 9010254 | 9/1990 | WIPO . | |

OTHER PUBLICATIONS

Fouassier, et al., "Polymerisation Induite Sous Irradiation Laser Visible", Makromol. Chem. 192, 1307–1315 (1991).

Kitamura, "Photopolymerizable Compositions for Printing Plates and Photoresists", CA 112:281186v (1990).

Amt–Guerri et al., "Synthesis and Spectroscopic Properties of New Rose Bengal and Eosin Y Derivatives", *Chem. Abs.* 112:236887b (1990).

Amt–Guerri et al., "Singlet Oxygen Photogeneration by Ionized and UnIonized Derivatives of Rose Bengal and Eosin Y in Diluted Solutions" *Photochem. and Photobio.* 53:199–210 (1990).

Flossman et al., "Mechanism of the color reaction of DNA and 2-deoyribose with Orcin", *Chem. Abs.* 76:46433r (1972).

CA107(25): 228304r, "The Raising and Characterization of Antibodies to Salicylates", Bennett, et al. Abstract only.

J. Org. Chem., vol. 57, "Xanthenes: Fluorone Derivatives" Shi, et al, pp. 4418–4421, Jul. 1992.

CA105: 80656t, "Novel Radical Couplings in the Photo Reduction of Xanthenoid Dyes with Tribenzyl–amine", Phillips, et al, J. Chem. Soc. Per. Trans. (4) pp. 671–673, 1986.

Hobbs et al., "Preparation of (aminoalkynyl) nucleotides as Intermediates for Fluorescent Chain Terminators for DNA Sequencing", *Chem. Abs.* 109:93540h (1988).

Janjie et al., "Multiligand Interactions at the Combining Site of Antifluorescyl Antibodies, Molecular Recognition and Connectivity", Journal Amer. Chem. Soc. 111:6374–6377 (1989).

Sapovalov, "Study of spectral and acid–base properties of Tetrabromo hydroxyphenyl xantherone" *Chem. Abs.* 115:246974d.

Shen, "A study on 6–hydroxyfluorone (Using a Modified PPP–CT Method)," *Chem. Abs.* 107:15635d.

Wang et al., "Study on a new chromogenic reagent 9-[4-(3-carboxy-4-hydroxy)phenylazo]fluorone and its application", *Chem. Abs.* 115:246974d.

H. J. Timpe "Photoinitiator Systems for Concurrent Radical and Cationic Polymerization", Pure & Applied Chemistry, vol. 60, No. 7, pp. 1033–1038 Jul. 1988.

*Primary Examiner*—Susan W. Berman
*Attorney, Agent, or Firm*—Thompson Hine & Flory LLP

[57] ABSTRACT

The present invention relates to a novel class of compounds which absorb light at wavelengths greater than 350 nm and are useful as fluorescers or as photoinitiators. The present invention provides compounds of the formulas (I) and (II) and their equivalents (the nomenclature of the compounds used herein is based on the numbering of positions as shown in formula (I)):

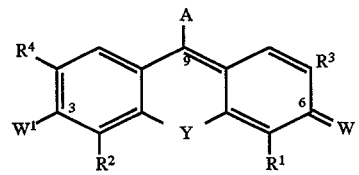

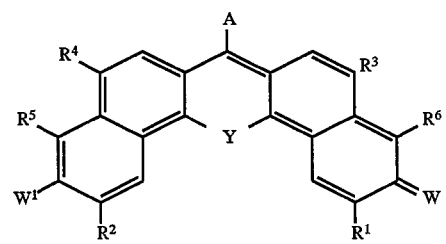

where: when W is =O, $W^1$ is hydrogen or —$OR^9$ and when W is =$NR^+_2$, W is hydrogen or —$NR_2$, A is hydrogen, alkenyl, alkyl or an election withdrawing group, and the remaining groups are as defined in the disclosure.

26 Claims, No Drawings

U.S. PATENT DOCUMENTS

| | | | |
|---|---|---|---|
| 4,735,632 | 4/1988 | Oxman et al. | 522/25 |
| 4,772,530 | 9/1988 | Gottschalk et al. | 430/138 |
| 4,828,583 | 5/1989 | Oxman et al. | 51/295 |
| 4,868,092 | 9/1989 | Kawabata et al. | 430/281 |
| 4,988,607 | 1/1991 | Ali | 522/25 |
| 5,096,530 | 3/1992 | Cohen | 156/229 |
| 5,137,800 | 8/1992 | Neckers et al. | 430/281 |

CATIONIC POLYMERIZATION

CROSS-REFERENCE TO RELATED APPLICATIONS

This application is a continuation-in-part of U.S. application Ser. No. 07/881,048 filed May 11, 1992, now abandoned, and 07/772,103 filed Oct. 7, 1991, now abandoned, which in turn is a continuation-in-part of Ser. No. 07/756,611 filed Sep. 9, 1991, now abandoned, which in turn is a continuation-in-part of Ser. No. 07/702,886 filed May 20, 1991, now abandoned.

GOVERNMENT RIGHTS

This invention was made with Government support under Grant N00014-91-J-1921 awarded by the Department of the Navy. The Federal Government has certain rights in the inventions disclosed herein.

BACKGROUND OF THE INVENTION

The present invention relates to novel photosensitive compositions and to photosensitive materials employing them. More particularly, it relates to compositions which are photohardenable by cationic polymerization.

Significant advances in UV curing based on the cationic polymerization of epoxy resins and in photoimaging technology based on photochemically induced acidolysis have been made following the discovery of thermally stable and highly efficient cationic photoinitiators such as diaryliodonium, triarylsulfonium and mixed-ligand arene cyclopentadienyl metal salts. Theoretically, diaryliodonium salts should have the highest efficiency among these initiators owing to their lower C-I bond energy and higher reactivity of dissociated species. However, the major absorption bands of these initiators fall at deep UV wave lengths (210–250 nm). The poor overlap of the absorption bands of iodonium salts with the emission spectra of commercially available medium and high-pressure mercury arc lamps has limited their efficiency and made them yield to thiophenoxy substituted triarylsulfonium salts in many important industrial applications. The latter have an additional absorption band at 300–400 nm and possess much higher efficiency.

Efforts have been made to extend the sensitivity of the initiators to longer wavelengths so that visible light could be used to initiate the cationic polymerization. Attempts have been made to synthesize new photoinitiators with longer wavelength absorption. It has been shown that the introduction of simple substitutes on the aryl rings does not markedly alter the spectral characteristics of iodonium salts. A diaryliodonium salt with a fluorenonyl group substituted on one aryl group has been synthesized. The formed compound has similar absorption and fluorescence spectra as fluorene and is the iodonium salt reported whose absorption wavelength goes to longest region. Despite its longer wavelength absorption, the rates of the polymerization initiated by this compound are not better than those of simple diaryliodonium photoinitiators.

Another technique for extending the photosensitivity of the photoinitiators to longer wavelength region is photosensitization. The photosensitization of iodonium salts by a wide variety of aromatic hydrocarbon, aromatic ketone, heterocyclic compounds and dyes has been studied. To some extent, these sensitizers can extend the sensitivity of iodonium salts to longer wavelengths, but few of them can provide visible light photoinitiation.

The photosensitization process can occur through three mechanisms: (1) energy transfer, (2) electron transfer and (3) free radical decomposition.

According to the energy transfer mechanism, an electronically excited photosensitizer is generated which interacts with the onium salt to promote it to its excited state while returning the photosensitizer to the ground state. Energy transfer photosensitization occurs for iodonium salts using photosensitizer with high triplet energy (>70 kcal/mol) and high oxidation potentials which prevent competing electron transfer processes form taking place.

A triplet energy of 70 kcal/mole is equivalent to a photon of 400 nm wavelength. The sensitizer must absorb far below 400 nm irradiation in order to intersystem-cross to its triplet state, which means the sensitizer must also be a UV absorbing species and the sensitizer can not extend the sensitivity of the UV initiator to visible light region. It has also been confirmed that even if a triplet iodonium salt is formed, the excited molecule is still unreactive toward bond cleavage.

In the electron transfer photosensitization, an electron is transferred from the excited photosensitizer to the onium salt. The result is that a photoredox reaction occurs in which a photosensitizer is oxidized to a cation-radical while the onium salt is reduced to a radical species. In subsequent steps, the diaryliodide radical collapses to iodoaromatic compound and an aryl radical. This mechanism of photosensitization requires that the initiator of cationic polymerization be derived from the photosensitizer, while in the direct photolysis the initiator originates from fragments derived from the photosensitizer. The following compounds have been found to possess a sensitizing effect on iodonium salt initiated cationic polymerization:

| Sensitizer | Excitation energy (nm) (T*) |
| --- | --- |
| Anthracene | 375 |
| Perylene | 432 |
| Phenothiazine | 500 |
| Xanthone | 385 |
| Thioxanthone | 432 |

Thioxanthone(TX) is a typical example of these sensitizers. Substituted thioxanthones exhibit a strong absorption band in the region of 250–270 nm as well as a weak band at 380–420 nm in the UV-visible region. These spectral features make them very attractive as photosensitizers. Although strong interactions in the excited states have been observed between TX and diphenyliodonium (DPI) salts, the rates of the cationic polymerizations of difunctional epoxy monomers were little enhanced compared to the same polymerizations carried out in the absence of a photosensitizer.

In photosensitization by free radical induced decomposition, the primary photochemical process occurs on the photosensitizer. Bond dissociation or hydrogen abstraction of the excited photosensitizer produces radicals in solution. Oxidation of these radicals by DPI produces cations which initiate the cationic polymerization. Photosensitization occurs not as a result of a direct interaction between the onium salt and the excited photosensitizer but as a secondary "dark" nonphotochemical reaction of the onium salt with the radical products of the photosensitizer.

Summarizing, although many efforts have been made to develop a visible light cationic initiating system, no satisfactory system has been found. The most significant visible sensitizers developed to date are the five amino substituted dyes reported by Crivello and Lam, "Dye-sentized Photoinitiated Cationic Polymerization," *Journal of Polymer Science*, Vol. 16, Polym. Chem. Ed., pp. 2441–2451 (1978).

U.S. Pat. No. 4,264,703 assigned to General Electric discloses that polymerization of a variety of polymerizable materials such as vinyl monomers, prepolymers, cyclic ethers, cyclic esters and cyclic organosiloxanes is effected by utilization of an initiator which includes aromatic halonium salt and, more particularly, diaryliodonium salts. These salts are described in greater detail in U.S. Pat. No. 4,264, 703 and by Crivello and Lam, "Diaryliodonium Salts. A New Class of Photoinitiators for Cationic Polymerization," *Macromolecules*, Vol. 10 No. 6, pp. 1307–1315 (1977). An alternative class of cationic initiators is triarylsulfonium salts as disclosed in Crivello and Lam, "Photoinitiated Cationic Polymerization with Triarylsulfonium Salts," *Journal of Polymer Science*, Vol. 17, pp. 977–999 (1979). The cationic polymerizations described in the aforementioned references are initiated by exposure to ultraviolet radiation.

The practical application of the above onium salts as cationic photoinitiators has been limited by their low absorptivity at wavelengths above 300 nanometers. However, it has been discovered that the spectral response of onium salts may be extended into the near ultraviolet and visible wavelengths by energy transfer and electron transfer/redox sensitization. An extensive review of this extension is described in Crivello, *Adv. in Polymer Sci.*, 62, 1 (1984). Crivello reports that through the use of certain photosensitizer-onium salt combinations, however, the process has tended to be extremely inefficient and hence of little practical utility for cationic photopolymerization.

Redox sensitization is known to occur by two distinct mechanisms. The first mechanism is direct electron transfer to release an acidic or cationic species. Examples of this mechanism have been described in U.S. Pat. No. 4,026,705 assigned to General Electric and in Crivello and Lam, "Dye-sensitized Photoinitiated Cationic Polymerization," *Journal of Polymer Science*, Vol. 16, Polym. Chem. Ed., pp. 2441–2451 (1978) and ibid. 17, p. 1059 (1979). As disclosed in these references an organic dye sensitizes the decomposition of onium salts, particularly diaryliodonium salts, upon exposure to radiation. Examples of dyes which are capable of photoexcitation as disclosed in the references include acridine and benzoflavin cationic dyes, benzophenone type basic dyes and perylene type neutral dyes. The quantum efficiency of the direct electron transfer is relatively low because there is a competing back electron transfer mechanism which reduces the amount of cationic species that are formed, and the spectral sensitivity has generally been limited to wavelengths less than 550 nm.

The second mechanism is indirect electron transfer wherein a free radical is photogenerated and subsequently undergoes electron transfer to the onium salt which releases an acid or cationic species. Examples of the indirect electron transfer mechanism are described in A. Ledwith, *Polymer*, 19, pp. 1217, 1219 (1978); Goetheis, ed. "Cationic Polymerization and Related Processes," Academic Press, p. 275 (1984); Crivello and Lee, *Macromolecules*, 14, 1141 (1981); Yagci et al., *Makromol. Chem. Rapid Commun.* 8, p. 209 (1987), and *Makromol. Chem. Symp.* 13 14, p. 161, (1988). Quantum yields greater than unity have been reported for the indirect electron transfer process. The photogenerated radicals from the sensitizer induce chain decomposition of onium salts and generate high yields of cations.

Few references describe or suggest the use of visible light free radical photoinitiators as the radical promoters for onium salt decomposition at wavelengths greater than 500 nm. Published European Application EP 0 408 227A1 to The Mead Corporation reports that certain dye-boranyl ion complexes can be combined with onium salts to provide viable cationic polymerization systems, throughout the visible spectrum. None of the references disclose or suggest the use of photoinitiators such as fluorones to extend initiation throughout the visible spectrum.

The above-described cationically polymerized materials have been used as moulding and extrusion resins, adhesives, caulks, coatings, printing inks, impregnated tapes, insulation, sealants, lubricants and the like.

SUMMARY OF THE INVENTION

As will become apparent from the detailed description hereinbelow, compositions which are photohardenable by cationic polymerization have been developed which include a cationically polymerizable compound, a xanthene or fluorone dye, a hydrogen donor and an iodonium, thiapyrylium, diazonium or ferrocenium salt. The resultant composition can be polymerized by cationic initiation upon exposure to radiation and particularly radiation extending into the visible spectrum. The photopolymerization follows a cationic mechanism, though radical species are also involved as intermediates. The detailed mechanism for the process is not clear. While not wishing to be bound by any specific theory, it is hypothesized that upon exposure of the xanthene or fluorone dye with visible light, radicals are formed by the interaction of the excited dye with either the amine (reductive bleaching) or the diaryliodonium salts (oxidative bleaching). These free radicals then transfer an electron to the onium salt and release a cation. Once such a cation is released, it attacks the monomer and initiates the polymer chain reaction. In the most common free radical reaction, the dye is an electron acceptor. In the presence of an onium salt and an amine, the dye is an electron acceptor with respect to the amine and an electron donor with respect to the onium salt. The rate of electron transfer from the dye to the onium salt is an order of magnitude faster than the rate of transfer from the amine to the dye.

In this system, an electron is transferred from the excited xanthene or fluorone dye to onium salts. Similar to the electron transfer photosensitization, a photoredox reaction occurs in which a photosensitizer is oxidized to a cation-radical while the onium salt is reduced to a radical species, e.g., a diaryliodide radical which collapses to iodoaromatic compound and an aryl radical. Different from the above process, the formed dye radicals will not initiate cationic polymerization (no positive charge), instead, the dye radicals and phenyl radicals may abstract hydrogen from the hydrogen donor (e.g., an aromatic amine with a hydrogen) to form secondary radicals ($\alpha$-aminoalkyl radicals). These secondary radicals may be oxidized by the onium cation to form radical cations which initiate the cationic polymerization. This is similar to photosensitization by free radical induced decomposition. Owing to the regeneration of radicals in the last step, a chain reaction may result.

A number of factors will affect the efficiency and success of the cationic system of the invention including the free energy of the electron transfer process, the efficiency of the oxidation of the radicals to cations, the electrophilicity of the cation, and the nucleophilicity of the hydrogen donor. The electrophilicity of the cation and the nucleophilicity of the hydrogen donor must be such that the cation is not trapped in an acid-base reaction. Free energy ($\Delta G$) may be estimated from the oxidation ($E_{ox}$) and excitation ($E_p$) energies of the photosensitizer and the reductive energy of the coinitiator ($E_{red}$).

$$\Delta G = E_{ox} - E_p - E_{red}$$

The more negative ΔG for the reaction, the more likely it is that the reaction will exhibit relatively larger quantum yields of photolysis and a high relative polymerization rate.

According to the present invention, a photohardenable composition is provided comprising: a cationically polymerizable compound, a xanthene or fluorone dye, a hydrogen donor and an onium salt capable of initiating cationic polymerization of said polymerizable compound upon exposure to actinic radiation. Preferred salts are iodonium, thiapyrylium, diazonium and ferrocenium salts. It is particularly preferred that the salt be an iodonium salt and most preferably a diaryliodonium salt. The cationically polymerizable compound may be an epoxy compound, a vinyl monomer, a vinyl prepolymer, a vinyl ether, a vinyl ether prepolymer, a cyclic ether, a cyclic ester, a cyclic sulfide, cyclic organosiloxanes, a cyclic acetal, and the like.

In a particular embodiment, a dual initiator system is possible which utilizes both cationic and free radical initiation mechanisms. Use of a dual initiator system enables rapid cure of stable monomeric materials and provides a wide latitude in the selection of polymer structure and properties.

Some of the applications in which compositions in accordance with the invention can be used are, for example, inks, adhesives, protective, decorative and insulating coatings, glass lamination, magnetic recording compositions, potting compounds, sealants, photoresists, wire insulation, can linings, textile coatings, laminates, impregnated tapes, printing plates, imaging materials and the like. In addition to being useful in photosensitive materials, the compositions of the present invention are also useful in a wide variety of other applications including photocurable inks and coatings, photoadhesives, printing plates, printed circuit fabrication, and other applications for photohardenable compositions.

DETAILED DESCRIPTION OF THE INVENTION

A wide range of xanthene or fluorone dyes may be used as photoinitiators in accordance with the invention. Some examples include Methylene Blue, rhodamine B, Rose Bengal, 3-hydroxy-2,4,5,7-tetraiodo-6-fluorone,5,7-diiodo-3-butoxy-6-fluorone, erythrosin B, Eosin B, ethyl erythrosin, Acridine Orange, 6'-acetyl-4,5,6,7-tetrachloro-2', 4', 5', 6', 7'-tetraiodofluorescein (RBAX), and the compounds of formulas (I)–(IV) below. Because these dyes exhibit different absorption bands and extinction coefficients, it is difficult to compare their efficiency. However, the quantum yield of triplet formation, the oxidation potentials and the conversion of cyclohexene oxide monomer to polymer of several dyes is provided in Table 1.

TABLE 1

| Photopolymerization of cyclohexene oxide (bulk) at 21° C.* with different photosensitizers | | | | | | |
|---|---|---|---|---|---|---|
| | | | | | Conversion (%) | |
| Dye | λ (nm) | Charge | φT | $E_{ox}$ | real | corrected |
| Rose Bengal | 548 | −2 | 0.76 | −1.0 | 20.2 | 13.3 |
| Eosin | 514 | −2 | 0.28 | −1.0 | 7.1 | 7.1 |
| Erythrosin | 525 | −2 | 0.62 | −1.0 | 21.8 | 34.6 |
| RBAX | 492 | 0 | <0.87 | −1.0 | 17.7 | 20.8 |

TABLE 1-continued

| Photopolymerization of cyclohexene oxide (bulk) at 21° C.* with different photosensitizers | | | | | | |
|---|---|---|---|---|---|---|
| | | | | | Conversion (%) | |
| Dye | λ (nm) | Charge | φT | $E_{ox}$ | real | corrected |
| THF | 538 | −1 | <0.87 | 1.34 | 12.5 | 11.3 |
| Methylene Blue | 656 | +1 | 0.58 | ~ | 4.6 | 0.9 |
| Rhodamine B | 556 | +1 | <0.01 | ~ | 9.5 | 5.0 |

*Dye Concentration: $2 \times 10^{-3}$ M;
4,4'Dimethyldiphenyliodonium tetrafluoroborate: $5 \times 10^{-2}$ M;
N,N-Dimethylaniline: $1.0 \times 10^{-2}$ M
Irradiation time: 4 hours The dyes useful herein include compounds of the formulas (I) and (II) and their equivalents (the nomenclature of the compounds used herein is based on the numbering of positions as shown in formula (I)):

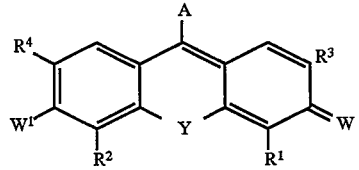

I

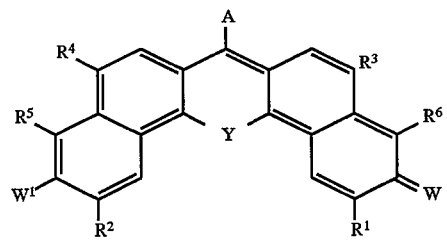

II where $R^1$, $R^2$, $R^5$ and $R^6$ are the same or different and represent a hydrogen atom or a halogen atom or $R^1$ and $R^2$ may combine to form a ring; $R^3$ and $R^4$ are the same or different and represent a hydrogen atom, a halogen atom, a benzoyl group, a group of the formula —L(CH$_2$)$_n$R$^8$ where n is 1 to 8, $R^8$ is hydrogen, hydroxy, amino, dialkylamino, —COR$^{16}$ or —COOR$^{14}$ where $R^{16}$ is hydrogen, chlorine, —COCl, C$_1$-C$_8$ alkyl, —NR$_2$, or aryl, and $R^{14}$ is hydrogen, C$_1$-C$_8$ alkyl, aryl, —COR, 2,4-dinitrophenyl, n-imido or —NR$_2$; and L is a direct bond or >C=O; W is =O or NR$_2^+$ where R is hydrogen or lower alkyl, when W is O, W$^1$ is hydrogen or —OR$^9$ where R$^9$ is hydrogen, C$_1$-C$_8$ alkyl, acyl or a group of the formula —(CH$_2$)$_n$R$^{10}$ where n is 1 to 8 and R$^{10}$ is amino, dialkylamino, hydroxy, acryloyl or methacryloyl and when W is NR$_2^+$, W$^2$ is hydrogen or —NR$^2$; Y is oxygen, sulfur selenium, tellurium, >C=O, or N—R$^{13}$ where R$^{13}$ is 4-methylphenyl, A is hydrogen, aryl, alkenyl, alkyl, or an electron withdrawing group (EWG); provided that at least one of R$^1$- R$^6$ is halogen.

In accordance with some of the preferred embodiments of the invention, the compounds of the invention more particularly include fluorone and pyronin Y derivatives of the formulae (III) and (IV):

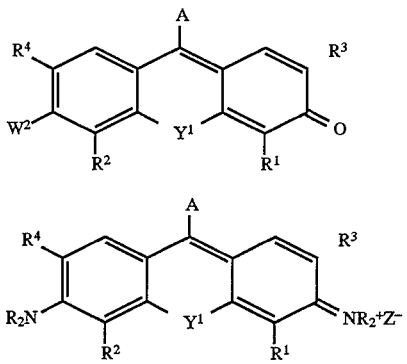

where A is selected from the group consisting of hydrogen, aryl, alkyl, alkenyl, alkynyl, dichlorotriazinylamino, and electron withdrawing groups (EWG) which are stronger electron withdrawing groups than a phenyl group or a halogen-substituted or a carboxyl-substituted phenyl group; $Y^1$ is oxygen, sulfur or >$NR^{13}$ where $R^{13}$ is 4-methylphenyl; R, and $R^1$- $R^4$ are defined as above; Z is a counter ion and $W^2$ is hydrogen or —$OR^9$ and $R^9$ is defined as above.

The compounds of the invention can be more particularly represented by the formula (V):

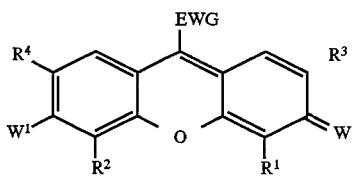

where $R^1$-$R^4$ may be the same or different and are defined as above; EWG is an electron withdrawing group selected from the group consisting of $COOR^{11}$, $COR^{12}$, $C(O)OCOR^{11}$, $CONR_2$, CN, $NO_2$, NCS, NCO, $SO_2R^{12}$, $SO_3R^{11}$, $SO_2NR_2$, $CX_3$; $R^{11}$ is hydrogen, alkyl, aryl, or aralkyl; $R^{12}$ is hydrogen, alkyl, aryl, or aralkyl, can be the same or different and is a halogen atom; and W and W' are selected from the group consisting respectively of O and O— and $NR_2^+$ and —$NR_2$ where R is defined as above.

In the photoinitiators of the invention preferably at least two of $R^1$- $R^6$ is a halogen atom and more particularly an iodine or bromine atom. A is hydrogen or cyano in a particularly preferred class of photonitiators. For use in photoinitiation $W^1$ is preferably butoxy or octyloxy. When $R^{10}$ is an acrylolyl or methacryloyl group, a polymermizable initiator is provided.

Respective examples of alkyl groups referenced with respect to the compounds of formula (I)–(VI) above are straight chain, branched chain and cyclic alkyl groups having 1 to 10 or more carbon atoms.

Representative examples of aryl groups include phenyl groups which may be unsubstituted or substituted by alkyl, chloro, $(CH_2)_p$ $COOR^{11}$, $(CH_2)pX$, $(CH_2)_pNR_2$, COONa where R, $R^{11}$ and X are defined as above and p is 0 to 6. Specific examples of aryl groups include phenyl; 2,3,4,5-tetrachlorophenyl, 2-carboxyphenyl sodium salt; 2,3,4,5-tetrachloro-6-carboxyphenyl sodium salt; and 2-carboxyphenyl Representative examples of aralkyl groups include aralkyl groups containing 7 to 20 carbon atoms such as benzyl, phenethyl, etc.

Representative examples of alkaryl groups include alkaryl groups containing 7 to 20 carbon atoms such as phenyl substituted at the ortho or para position by a straight chain or branched chain alkyl group having 1 to 6 carbon atoms.

Representative examples of alkenyl groups include alkenyl groups having 2 to 10 carbon atoms such as vinyl, allyl, 1-propenyl, 1-butenyl and 1,3-butadienyl.

Representative examples of alkynyl groups include alkynyl groups having up to 10 carbon atoms such as 1-propynyl, 1-butynyl, etc.

Representative examples or acyl groups are groups of the formula —$OCR^{17}$ where $R^{17}$ is an alkyl or an aryl group such as methyl and phenyl.

Representative examples of the halogen atoms include fluorine, chlorine, bromine and iodine and, more particularly, bromine and iodine.

Representative examples of the counter ion represented by Z include chloride, bromide, iodide, perchlorate when Z is an anion and monovalent ions such as $K^+$, $Na^+$, ammonium, phosphonium, etc. when Z is a cation. When W/W' is O/O⁻, Z may be hydrogen.

Representative examples of electron withdrawing groups include $COOR^{11}$, $COR^{12}$, $C(0)OCOR^{11}$, $CONR_2$, CN, $NO_2$, NCS, NCO, $SO_2R^{12}$, $SO_3R^{11}$, $SO_2NR_2$, $CX_3$ where X, $R^{11}$ and $R^{12}$ are defined above.

Representative examples of dyes in accordance with the invention include:

1. 5,7-diiodo-3-methoxy-6-fluorone (DIMF)
2. 5,7-diiodo-3-ethoxy-6-fluorone (DIEF)
3. 5,7-diiodo-3-butoxy-6-fluorone (DIBF)
4. 5,7-diiodo-3-octoxy-6-fluorone (DIOF)
4a. 4,5-diiodo-3-hydroxy-6-fluorone
5. 9-cyano-5,7-diiodo-3-methoxy-6-fluorone (CDIMF)
6. 9-cyano-5,7-diiodo-3-ethoxy-6-fluorone (CDIEF)
7. 9-cyano-5,7-diiodo-3-butoxy-6-fluorone (CDIBF)
8. 9-cyano-5,7-diiodo-3-octoxy-6-fluorone (CDIOF)
9. 3-hydroxy-2,4,5,7-tetraiodo-6-fluorone (TIHF)
10. 3-hydroxy-2,4,5,7-tetrabromo-6-fluorone (TBHF)
11. 3-hydroxy-2,4,5,7-tetrachloro-6-fluorone (TCHF)
12. 3-hydroxy-2,4,5,7-tetrafluoro-6-fluorone (TFHF)
13. 9-cyano-3-hydroxy-2,4,5,7-tetraiodo-6-fluorone (TIHCF)
14. 9-cyano-3-hydroxy-2,4,5,7-tetrabromo-6-fluorone (TBHCF)
15. 9-cyano-3-hydroxy-2,4,5,7-tetrachloro-6-fluorone (TCHCF)
16. 9-cyano-3-hydroxy-2,4,5,7-tetrafluoro-6-fluorone (TFHCF)
17. 3-hydroxy-4,5,7-triiodo-2-octanoyl-6-fluorone
18. 9-cyano-3-hydroxy-4,5,7-triiodo-2-octanoyl-6-fluorone
19. 3-hydroxy-4,5,7-triiodo-2-octanoyl-6-fluorone
20. 9-cyano-3-hydroxy-4,5,7-triiodo-2-octyl-6-fluorone
21. 3-hydroxy-2,4,5,7-tetraiodo-6-thiafluorone
22. 3-hydroxy-4,5,7-triiodo-2-pentanoyl-6-fluorone
23. 9-cyano-3-hydroxy-4,5,7-triiodo-2-pentanoyl-6-fluorone
24. 3-hydroxy-4,5,7-triiodo-2-pentyl-6-fluorone
25. 9-cyano-3-hydroxy-4,5,7-triiodo-2-pentyl-6-fluorone
26. 2,7-di-t-butyl-4,5-diiodo-3-hydroxy-6-fluorone
27. 9-cyano-2,7-di-t-butyl-4,5-diiodo-3-hydroxy-6-fluorone
28. 7-benzoyl-2,4,5-triiodo-3-hydroxy-6-fluorone Potentially useful onium salts include iodonium salts; thiapyrylium salts; diazonium salts; and ferrocenium salts and, more particularly, diaryliodonium hexaflurophosphates, diaryliodonium arsenates and diaryliodonium antimonates; and phenyldiazonium salts such as $ArN_2^+BF_4^-$.

The counter ion of the onium salts, usually a nonnucleophilic semimetal complex, plays a decisive role in determining the rate of polymerization. In the case of the SbF6⁻ the rate of polymerization is so fast that it is difficult to measure, while for the $BF_4^-$ salt it was considerably slower. The general order of reactivity was found to be $SbF_6^-$ >$AsF_6^-$>$PF_6^-$>$BF_4^-$. One can also use chlorides, bromides, iodides, sulfates, etc. Since the photolysis of diaryliodonium salts with common cations but different anions disclosed that the rates of photodecomposition of the salts are independent of the cationic portion of the salts[19], the observed polymerization rates must then be dependent only on the nature of the anion. This effect has been explained on the basis of the degree of separation in the ion pair. The larger the negatively charged ion is, the more loosely it is bound and the more active the propagating cationic species is in the polymerization.

Where the onium salt is an iodonium salt it can be represented by the formula:

$$[R^{25}{}_aR^{26}{}_bI]^{+c} [MQ_d]^{-(d-e)} \qquad (VI)$$

where $R^{25}$ is a monovalent aromatic organic radical; $R^{26}$ is a divalent organic radical, M is a metal, such as antimony, iron, tin, bismuth, aluminum, gallium, indium, titanium, zirconium, scandium, vanadium, chromium, manganese, cerium, or rare earth elements, such as lanthanides and actinides, or a metaloid, such as carbon, nitrogen, phosphorus, boron, or arsenic, and Q is a halogen, alkyl, aryl, or alkyl, or equivalent radical, a and b are whole numbers equal to 0, 1 or 2, c is equal to (d–e), e is equal to the value of M and in an integer equal to 2 to 7 inclusive, and d is an integer of exp to 8.

Radicals included by $R^{25}$ can be the same or different aromatic, carbocyclic or heterocyclic radicals having from 6 to 20 carbon atoms, which can be substituted on the ring with from 1 to 4 monovalent radicals selected from $C_{(1-18)}$ alkoxy, $C_{(1-18)}$ alkyl, nitro, chloro, etc., $R^{25}$ is more particularly phenyl, chlorophenyl, nitrophenyl, methoxyphenyl, pyridyl, etc. Radicals included by $R^{26}$ are divalent radicals such as

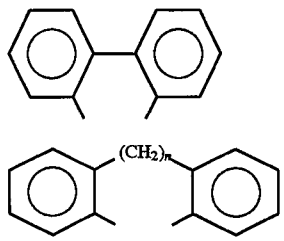

where n is 1–2, etc. Metal or metalloids included by M of formula (VI) are transition metals such as Sb, Fe, Sn, Bi, Al, Ga, In, Ti, Zr, Sc, V, Cr, Mn, Cs, rare earth elements such as the lanthanides, for example, Cd, Pr, Nd, etc., actinides, such as Th, Pa, U, Np, etc. and metalloids such as B, P, As, etc. Complex anions included by $MQ_{d}^-{}_{(d-e)}$ are, for example, $BF_4^-$, $PF_6^-$, $AsF_6^-$, $SbF_6^-$, $FeCl_4^-$, $SnCl_6^=$, $SbCl_6^-$, $BiCl_3^-$, etc. Simple anions such as $Cl^-$, $Br^-$, $I^-$, $SO_4^=$, etc. are also helpful.

Halonium salts (especially iodonium salts) included by formula (VI) are, for example,

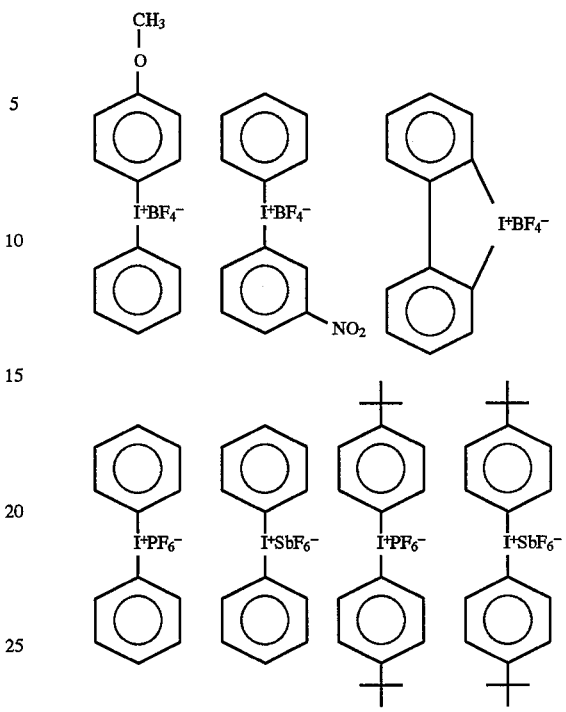

The halonium salts of formula (VI) can be made by the procedures described by O. A. Ptitsyna, M. E. Pudecva, et al., Dokl, Adad Nauk, SSSR, 163, 383 (1965); Dokl, Chem., 163, 671 (1965). F. M. Beringer, M. Drexler, E. M. Gindler, J. Am. Chem. Soc., 75, 2705 (1953). J. Collette, D. McGreer, R. Crawford, et al., J. Am. Chem. Soc. 78, 3819 (1956). Other aryliodonium salts include the polymeric iodonium salts which are described in U.S. Pat. No. 4,780,511 and are hereby incorporated by reference.

Representative examples of iodonium salts of formula (VI) include salts having the following structures: $C_nH_{2n+1}$, $C_6H_4I^+(C_6H_5)$, $(C_nH_{2n+1}C_6H_4)_2$ $I^+$, $(C_nH_{2n+1}OC_6H_4)I^+$ $(C_6H_5)$ and $(C_nH_{2n+1}OC_6H_4)_2I^+$ where n=8 to 12.

Particularly preferred iodonium salts are the aryliodonium salts, and most preferably, the diaryliodonium salts such as 4,4'-dimethyldiphenyliodonium tetrafluoroborate and (4-octyloxyphenyl) phenyliodonium hexafluoroantimonate (OPPI).

Coinitiators useful in the present invention can be selected from among those known in the art and, more particularly, from known hydrogen donating coinitiators. Non-nucleophilic amines such as aromatic amines of low basicity are particularly useful in the invention.

The relative efficiency of the coinitiator in cationic polymerization not only depends on the efficiency of radical generation, but also on the efficiency of the oxidation of the radicals to cations as well as on the efficiency of the cation to initiate the cationic polymerization. The coinitiator must have a low basicity and low nucleophilicity as well as certain other properties not required in free radical initiated polymerization. If the coinitiator is too basic, it will deactivate the cationic center responsible for initiation. Only aromatic amines with α hydrogens are capable of initiating ring opening polymerization of cyclohexene oxide. Aliphatic amines, aromatic amines without α hydrogens and non-amine hydrogen donors are incapable of the initiation with cyclohexene oxide.

Representative examples of N,N-dialkylanilines useful in the present invention are 4-cyano-N,N-dimethylaniline, 4-acetyl-N,N-dimethylaniline, 4-bromo-N,N-dimethylaniline, 4-methyl-N,N-dimethylaniline, 4-ethoxy-N,N-dimethylaniline, N,N-dimethylthioanicidine, 4-amino-N,N-dimethylaniline, 3-hydroxy-N,N-dimethylaniline, N,N,N'N'-tetramethyl-1,4-dianiline, 4-acetamido-N,N-dimethylaniline, 2,6-diethyl-N,N-dimethylaniline, N,N,2,4,6-pentamethylaniline(PMA) p-t-butyl-N,N-dimethylaniline and N,N-dimethyl-2,6-diisopropyl aniline. Also useful as coinitiators are N-phenylglycine and N,N-dimethyltoluidine.

The invention is not limited to the use of amines or aromatic amines as hydrogen donors. Other compounds present in the composition may be capable of functioning as a hydrogen donor. For example, many monomers are capable of acting as hydrogen donors and compositions containing these compounds may be used effectively with or without amines. A specific example of such monomer are certain cycloaliphatic epoxides.

There are hundreds of monomers which can be polymerized by means of a cationic mechanism. These monomers can be classified according to their functionality. They include cyclic ethers, cyclic formals and acetals, vinyl ethers, and epoxy compounds. These monomers can be made monofunctional, difunctional and multifunctional. They may also be large molecular weight prepolymers and oligomers. Examples of cationically polymerizable compounds include epoxy compounds, vinyl or allyl monomers, vinyl or allylic prepolymers, vinyl ethers, vinyl ether functional prepolymers, cyclic ethers, cyclic esters, cyclic sulfides, melamine formaldehyde, phenolic formaldehyde, cyclic organosiloxanes, lactams and lactones, cyclic acetals and epoxy functional silicone oligomers.

Epoxy monomers are the most important class of polymerizable substrates. These materials are readily available as commodity items, and the resulting cured polymers possess excellent dimensional and thermal stability as well as superior mechanical strength and chemical resistance. They are widely used in the coating, painting and adhesives industry. The relationship between structure and reactivity in epoxy monomers is a complex function of several factors. The reactivity of an epoxy monomer is not only determined by the electronic nature of its particular epoxy group, its steric accessibility and the initiating species used but also by properties like the basicity, the nucleophilicity of other functional groups which coexist in the monomer. In general, epoxidized diolefins are most reactive, followed by epoxidized diolefins containing acetal and ester linkage followed finally by diglycidyl ethers.

Examples of cationically polymerizable epoxy compounds described in the literature include any monomeric, dimeric or oligomeric or polymeric epoxy material containing one or a plurality of epoxy functional groups. Examples of polymerizable epoxy compounds include bisphenol-A-diglycidyl ether, trimethylene oxide, 1,3-dioxolane, 3,4-epoxycyclohexylmethyl-3',4'-epoxycyclohexyl carboxylate, phenyl glycidyl ether, 4-vinylcyclohexene dioxide, limonene dioxide, cycloaliphatic epoxides such as 1,2-cyclohexene oxide, epichlorohydrin, glycidyl acrylate, glycidyl methacrylate, styrene oxide, allyl glycidyl ether, etc. Resins which result from the reaction of bisphenol A (4,4-isopropylidenediphenol) and epichlorohydrin, or from the reaction of low molecular weight phenol-formaldehyde resins (Novolak resins) with epichlorohydrin have been used alone or in combination with an epoxy containing compound.

In addition, polymerizable epoxy compounds include polymeric materials containing terminal or pendant epoxy groups. Examples of these compounds are vinyl copolymers containing glycidyl acrylate or methacrylate as one of the comonomers. Other classes of epoxy containing polymers amenable to cure have also been described in the literature and include epoxy-siloxane resins, epoxy-polyurethanes and epoxy-polyesters. Such polymers usually have epoxy functional groups at the ends of their chains. Epoxy-siloxane resins and the method for making them are more particularly shown by E. P. Plueddemann and G. Ganger, J. Am. Chem. Soc. 81 632-5 (1959), and in Crivello et al., Proceeding ACS, PMSE, 60, 217 (1989).

As described in the literature, epoxy resins can also be modified in a number of standard ways such as reactions with amines, carboxylic acids, thiols, phenols, alcohols, etc. as shown in U.S. Pat. Nos. 2,935,488; 3,235,620; 3,369,055; 3,379,653; 3,398,211; 3,403,199; 3,563,850; 3,567,797; 3,677,995, etc. Further examples of epoxy resins are shown in the Encyclopedia of Polymer Science and Technology, Vol. 6, 1967, Interscience Publishers, New York, pp. 209–271.

Examples of vinyl or allyl organic monomers which have been used in the literature in the practice of the cationic polymerization include, for example, styrene, vinyl acetamide, methyl styrene, isobutyl vinyl ether, n-octyl vinylether, acrolein, 1,1-diphenylethylene. R-pinene; vinyl arenes such as 4-vinyl biphenyl, 1-vinyl pyrene, 2-vinyl fluorene, acenapthylene, 1 and 2-vinyl napthylene; 9-vinyl carbazole, vinyl pyrrolidone, 3-methyl-1-butene; vinyl cycloaliphatics such as vinylcyclohexane, vinylcyclopropane, 1-phenyvinylcyclopropane; dienes such as isobutylene, isoprene, butadiene,, 1,4-pentadiene, 2-chloroethyl vinyl ether, etc.

Some of the vinyl organic prepolymers which have been described are, for example, $CH_2=CH-O-(CH_2O)_n-CH=CH_2$, where n is a positive integer having a value up to about 1000 or higher; multi-functional vinylethers, such as 1,2,3-propane trivinyl ether, trimetheylolpropane trivinyl ether, polyethyleneglycol divinylether (PEGDVE), triethyleneglycol divinyl ether (TEGDVE), vinyl ether-polyurethane, vinyl ether-epoxy, vinyl ether-polyester, vinyl ether-polyether and other vinyl ether prepolymers such as 1,4-cyclohexane dimethanol-divinylether, commercially available from GAF and others, and low molecular weight polybutadiene having a viscosity of from 200 to 10,000 centipoises at 25° C., etc.

A further category of cationically polymerizable materials are cyclic ethers which are convertible to thermoplastics. Included by such cyclic ethers are, for example, oxetanes such as 3,3-bis-chloromethyloxetane alkoxyoxetanes as shown by U.S. Pat. No. 3,673,216; oxolanes such as tetrahydrofuran, oxepanes, oxygen containing spiro compounds, trioxane, dioxolane, etc.

In addition to cyclic ethers, there are also included cyclic esters such as lactones, for example, propiolactone, cyclic amines, such as 1,3,3-trimethylazetidine and cyclic organosiloxanes, for example. Examples of cyclic organosiloxanes include hexamethyl trisiloxane, octamethyl tetrasiloxane, etc. Cyclic acetals may also be used as the cationic polymerizable material. Examples of epoxy functional silicone oligomers are commercially available from General Electric and are described in ACS PMSE Proceeding 1989, Vol. 60, pp. 217, 222.

Because the photoinitiator generates both free radicals and cations, it is possible to utilize a combination of free radical polymerizable and cationic polymerizable monomers. Examples of free radical polymerizable monomers include both monomers having one or more ethylenically unsaturated groups, such as vinyl or allyl groups, and polymers having terminal or pendant ethylenic unsaturation. Such compounds are well known in the art and include acrylic and methacrylic esters of polyhydric alcohols such as trimethylolpropane, pentaerythritol and the like, and acrylate or methacrylate terminated epoxy resins, acrylate or methacrylate terminated polyesters, etc. Representative examples include ethylene glycol diacrylate, ethylene glycol dimethacrylate, trimethylolpropane triacrylate (TMPTA), pentaerythritol tetraacrylate, pentaerythritol tetramethacrylate, dipentaerythritol hydroxypentacrylate (DPHPA), hexanediol-1, 6-dimethacrylate, and diethyleneglycol dimethacrylate. For example, it is contemplated that a mixture of styrene or an acrylate and a vinyl ether or epoxy could be used as a starting material.

Examples of other materials which are both cationically and free radically cured include glycidyl methacrylates, epoxy acrylates, acrylated melamine formaldehyde and epoxidized siloxanes. The simultaneous utilization of a cationically and free radical curable system enables rapid curing to be accomplished and provides a wide latitude in the design of product performance. For example, when a solution of acrylate and epoxy acrylate is used as the dual curable composition, film properties ranging from flexible to rigid can be produced and desired adhesive characteristics can be produced by selection of designed ratios of functional groups. The epoxy functionality provides high temperature resistance, excellent adhesion and reduced oxygen sensitivity whereas the acrylate functionality provides rapid curing speed, excellent weatherability, flexibility and desirable viscosity. Other examples of dual curable systems will be envisioned and appreciated by those skilled in the art.

Solvents may be necessary to dissolve the photoinitiator if the photoinitiator is not sufficiently soluble in the monomer. Solvents may also be used to shift the absorption spectrum to tune the sensitivity of the composition. Some examples of useful solvents are N-vinylpyrrolidone and nitrobenzene. Other useful solvents can be identified readily.

The nature of the monomer or polymerizable material, the amount of the xanthene or fluorone dye and onium salt in photohardenable compositions in accordance with the present invention will vary with the particular use of the compositions, the emission characteristics of the exposure sources, the development procedures, the physical properties desired in the polymerized product and other factors. With this understanding, compositions in accordance with the invention will generally fall within the following compositional ranges in parts by weight (based on 100 parts total).

| Polymerizable compound | 50 to 99.7 |
|---|---|
| Xanthene or fluorone dye | .05 to 1.0 |
| Onium Salt | up to 5.0 |
| amine | 0 to 1.0 |

Compositions in accordance with the invention more typically are anticipated to have the following formulation:

| Polymerizable compound | 50 to 97.5 |
|---|---|
| Xanthene or fluorone dye | .05 to 0.5 |
| Onium Salt | 1.0 to 3.0 |
| Amine | 0 to 0.5 |

The photohardenable compositions of the present invention can be coated upon a support in a conventional manner and used in making a photoresist or in photolithography to form an oleophilic polymer image. Development of photohardenable compositions in accordance with the invention is conducted in an otherwise known or conventional manner, e.g., a solvent for the unpolymerized monomer may be used to remove the photohardenable composition in the unexposed areas.

The photohardenable composition of the invention may also be advantageous for use in the three dimensional modeling process taught in U.S. Pat. No. 4,575,330 to Hull. Due to the thicker depth of cure that is possible, models may be prepared in larger cross-sectional increments. This should reduce the total time required for the model building process. Another advantage which the claimed compounds bring to three dimensional modeling is higher green strength.

Generally, fluorones in accordance with the invention absorb at about 350 to 670 nm. It is anticipated that sensitivity can be extended to longer wavelengths by substituting electron donating groups for A. Depending upon the extinction coefficient, compositions and photosensitive materials in accordance with the invention can be exposed to any source which emits in this range and particularly an He/Ne laser, a mercury arc lamp, any of the fusion system 'doped' lamps, a tungsten halogen lamp or other visible light sources.

The syntheses of fluorones in accordance with the present invention are illustrated in U.S. patent application Ser. No. 07/772,103 and European Patent Application No. 0 515 133 A2.

EXAMPLES

EXAMPLE 1

A cyclohexene oxide solution containing $2 \times 10^{-3}$ M ethyl erythrosine, $5 \times 10^{-2}$ M diphenyliodonium hexafluoroantimonate, $5 \times 10^{-2}$ M N,N,2,4,6-pentamethylaniline in a test tube was irradiated with visible light (>520 nm) from a tungsten lamp in a merry-go-round holder which was totally immersed in a cooling water bath tub. The solution completely cured after irradiation for 10 minutes.

EXAMPLE 2

Photocurable compositions were prepared using 75 parts cycloaliphatic diepoxide and 25 parts polyol with the results indicated below:

A. Using a 75 watt dental lamp at a distance of 1 inch (approx. 400 mw/cm$^2$), a 0.4% DIEF, 2% DPI sample was completely cured in a 10 mil thick film with a tack-free surface after a 60 second exposure to the sam elight source, but a 2% DPI control did not cure at all.

B. Uisng a 75 watt dental lamp w/blue filter at a distance of 1 inch (approx. 50 mw/cm$^2$), 0.4% DIEF, 2% DPI sample was completely cured in a 10 mil thick film with a tack-free surface after a 60 second exposure. This time neither the 2% triaryl sulfonium control nor the 2% DPI control cured at all after a 60 second exposure to the dental lamp.

C. A 0.4% DIEF, 2% DPI sample was irradiated in the focal pont of a 360 watt overhead projector (300 mw/cm$^2$) for 60 seconds and was completely cured in a 10 mil thick film and had a tack-free surface. The control smaples (2% triaryl sulfonium and 2% DPI) did not cure after 60 seconds of exposure under the same conditions.

D. 0.2% N,N-dimethyl diisopropyl aniline (DIDMA) was added to the 0.4% DIEF, 2% DPI mixture. The samples were fully cured in 10 mil thick films after being exposed to the 75 watt dental lamp for 60 seconds at a distance of 1 inch (approx. 400 mw/cm$^2$). These samples were slightly softer than those produced in example 2 part A, but the bleaching of the samples was greatly enhanced. This demonstration of bleaching provides a benefit for some markets where minimum color is desired. In addition, bleaching is expected to provide greater depth of cure.

D. A 10 mil thick sample containing 2% DIEF and 2% DPI was completely cured at a line speed of 10 ft/min. using a 300 WPI Fusion "Q" bulb. A 10 mil thick control sample containing 2% DPI only cures to a thickness of 5 mils at 10 ft/min.

EXAMPLE 3

Photocurable compositions were prepared using 75 parts cycloaliphatic diepoxide and 25 parts polyol. Variations in curing were then performed with the results indicated below:

A. A sample containing 0.1% DIEF and 2% DPI, and controls containing either 2% DPI or 2% triaryl sulfonium were irradiated in ⅛" thick plugs using a 75 watt dental lamp at 0 inches (approx. 3 W/cm$^2$). The sample with DIEF was fully cured after 60 seconds. However, the 2% triaryl sulfonium was only cured on the surface, and the 2% DPI sample wasn't cured at all. The implications of this would indicate that depth of cure is possible only in the dye w/DPI sample.

B. Additionally, fillers were added to a sample containing 0.05% DIEF and 2% DPI and tested for depth of cure capabilities. Both a 70% glass bead filled mixture and a 50% BaSO$_4$ filled mixture were cured to a thickness of ⅛" after a 1 minute exposure in the focus of the Fusion "Q" bulb. Again two controls were tested, one containing 2% triaryl sulfonium and the other containing 2% DPI. In each case the samples only cured on the surface (approx. 15–20 mils thick or ¹⁄₅₀") after 60 seconds with the same loading of fillers.

EXAMPLE 4

Photocurable compositions were prepared using triethylene glycol divinyl ether with the results indicated below.

A. At ¼ inch from the sample, a 0.2% DIBF, 2.5% OPPI mixture cures in 4 seconds using a 75 W dental lamp with blue filter installed (approx. 260 mw/cm$^2$). The reaction is exothermic, resulting in a darkened material which fumes upon curing. Control samples of 2% triaryl sulfonium and 2.5% OPPI without dye are uncured after 60 seconds at the same conditions.

B. At 1 inch from the sample, a 10 mil thick sample of the 0.2% DIBF, 2.5% OPPI mixture cures in 11–12 seconds, using a 75 watt dental lamp with blue filter installed (approx. 50 mw/cm$^2$). The reaction is again exothermic and the polymer darkens."

C. The 0.2% DIBF, 2.5% OPPI sample was laid down in 10 mil thick films which were then cured using a 300 WPI Fusion "Q" bulb. The samples are fully cured with darkened surfaces at line speeds up to 50 ft/min.

D. ¼ inch plugs of 0.2% DIBF, 2.5% OPPI mixture cure with the visible light from an overhead projector (approx. 400 mw/cm$^2$), after 23 seconds forming a soft, spongy, dark polymer. The reaction is exothermic. The controls (2.5% OPPI without dye or 2% triaryl sulfonium) do not cure after 2 minutes of exposure.

EXAMPLE 5

Photocurable compositions were prepared using 1,4-cyclohexane-dimethanol divinyl ether with the results discussed below:

A. At ½ inch from the sample, a 0.2% DIBF, 2.5% OPPI film 5 mils thick is fully cured after 6 seconds of exposure from a 75 watt unfiltered dental lamp (approx. 1 watt/cm$^2$). The surface is tack-free and the polymer clear and colorless. The 2.5% OPI control (without dye) does not cure at all. The 2% triaryl sulfonium starts to cure after 60 seconds, but the polymer formed is no bigger than a small dot."

B. At 1 inch from sample, a 0.2% DIPF, 2.5% OPPI film 5 mils thick is mostly cured, with a slightly wet surface after a 60 second exposure from the 75 watt dental lamp (approx. 40 mw/cm$^2$). Control samples (2.5% OPPI or 2% triaryl sulfonium) do not cure at all under the same conditions.

C. When the blue filter is installed in the dental lamp, neither the 0.2% DIBF, 2.5% OPPI sample, nor the two control samples cure after 60 seconds of exposure at a distance of ¼ inch (approx. 200 mw/cm$^2$).

D. The 0.2% DIBF, 2.5% OPPI sample was laid down in 10 mil thick films which were than cured using a 300 WPI Fusion "Q" bulb. The samples are fully cured with darkened surfaces at line speeds up to 50 ft/min.

EXAMPLE 6

Photocurable compositions were prepared using an epoxy functional silicone with the photoinitiator shown in the table and the onium salt OPPI.

| Initiator | CONC. | Onium % | Conditions* | Exp. Time | Comments** |
| --- | --- | --- | --- | --- | --- |
| DIBF | 0.00 wt % | 2.5% OPPI | DL ½" | 60 sec | DNC |
| DIBF | 0.05 wt % | 2.5% OPPI | DL ½" | 30 sec | FC, TF, ½" diameter |
| DIBF | 0.10 wt % | 2.5% OPPI | DL ½" | 60 sec | FC, TF, ¹⁷⁄₃₂" diameter |
| DIBF | 0.15 wt % | 2.5% OPPI | DL ½" | 60 sec | FC, TF, ⅝" diameter |
| DIBF | 0.00 wt % | 2.5% OPPI | DLBF ½" | 4 min | DNC |
| DIBF | 0.05 wt % | 2.5% OPPI | DLBF ½" | 4 min | DNC |
| DIBF | 0.10 wt % | 2.5% OPPI | DLBF ½" | 4 min | DNC |
| DIBF | 0.15 wt % | 2.5% OPPI | DLBF ½" | 4 min | DNC |
| TIHF | 0.05 wt % | 2.5% OPPI | DLBF ½" | 4 min | DNC |
| TIHF | 0.05 wt % | 2.5% OPPI | DL ½" | 60 sec | FC, TF, ⅜" diameter |
| TIHF | 0.05 wt % | 2.5% OPPI | DL ½" | 2 min | FC, TF, ⁹⁄₁₆" diameter |
| DIBF | 0.05 wt % | 2.5% OPPI | DLPC ½" | 2 min | FC, TF, ⁹⁄₁₆" |

| Initiator | CONC. | Onium % | Conditions* | Exp. Time | Comments** |
|---|---|---|---|---|---|
| DIBF | 0.10 wt % | 2.5% OPPI | DLPC ½" | 2 min | FC, TF, ¾" diameter |
| DIBF | 0.15 wt % | 2.5% OPPI | DLPC ½" | 2 min | FC, TF, ¹³⁄₁₆" diameter |
| DIBF | 0.15 wt % | 2.5% OPPI | DLPC ½" | 1 min | FC, TF, ¾" diameter |
| DIBF | 0.15 wt % | 1.5% OPPI | DLBF ½" | 4 min | MC, TF, ⅝" diameter |
| DIBF | 0.15 wt % | 1.5% OPPI | DLPC ½" | 1 min | FC, TF, ½" diameter |
| DIBF | 0.15 wt % | 1.5% OPPI | DLPC ½" | 2 min | FC, TF, ¾" diameter |

*DL = 75 W dental lamp
DLBF = 75 W dental lamp with blue filter
DLPC = 75 W dental lamp with ⅛" thick polycarbonate sheet
½" = light source is positioned one half inch away from the sample
**DNC = No cure;
FC = Fully Cured;
MC = Mostly Cured;
TF = Tack Free;
The diameter listed is that of the film produced by the light exposure. The magnitude of the diameter is an indication of the extent of reaction that the film has undergone; the larger the diameter, the more reactive the initiator system.

It is interesting to note that the above samples were also tested in thicker sections. It was found that those samples with a concentration of 0.05% DIBF or higher and 2.5% OPPI cured to a depth of ¼ inch after a 30 second exposure to the dental lamp at 0 inches away. The comparable control without dye does not cure.

Having described the invention in detail and by reference to preferred embodiments thereof, it will be apparent that modifications and variations are possible without departing from the scope of the invention defined in the appended claims.

What is claimed is:

1. A photohardenable composition which comprises a cationically polymerizable compound selected from the group consisting of epoxy compounds, vinyl ethers, vinyl ether functional prepolymers, cyclic ethers, cyclic esters, cyclic sulfides, melamine-formaldehyde, phenol-formaldehyde, cyclic organosiloxanes, lactams, lactones, cyclic acetals, and epoxy functional silicone oligomers; a dye represented by the Formula (I) or (II):

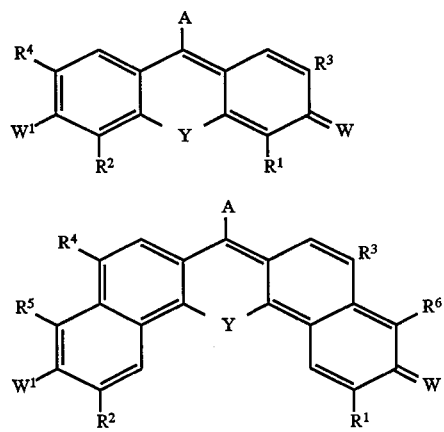

where $R^1$, $R^2$, $R^5$ and $R^6$ are the same or different and represent a hydrogen atom or a halogen atom and where $R^1$ and $R^2$ may combine to form a ring; $R^3$ and $R^4$ are the same or different and represent a hydrogen atom, a halogen atom, a benzoyl group, a group of the formula $—L(CH_2)_n R^8$ where n is 1 to 8, $R^8$ is hydrogen, hydroxy, amino, dialkylamino, $—COR^{16}$ or $—COOR^{14}$ where $R^{16}$ is hydrogen, chlorine, COCl, $C_1$-$C_8$ alkyl, $NR_2$, or aryl, and $R^{14}$ is hydrogen, $C_1$-$C_8$ alkyl, aryl, COR, $NR_2$; and L is a direct bond or $>C=O$; W is O or $>NR_2^+$ where R is hydrogen or lower alkyl, when W is O, $W^1$ is hydrogen or $—OR^9$ where $R^9$ is hydrogen, $C_1$-$C_8$ alkyl, acyl or a group of the formula $—(CH2)_n R^{10}$ where n is 1 to 8 and $R^{10}$ is amino, dialkylamino, hydroxy, acryloyl or methacryloyl and when W is $>NR_2^+$, $W^1$ is hydrogen or $—NR_2$; Y is oxygen, sulfur, selenium, tellurium, $>C=O$, or $>N—R^{13}$, where $R^{13}$ is 4-methylphenyl, A is hydrogen, aryl, alkenyl, alkynyl, dichlorotriazinylamino, alkyl, or an electron withdrawing group (EWG) which is a stronger electron withdrawing group than a phenyl group or a halogen-substituted or a carboxyl-substituted phenyl group; provided that at least one $R^1$-$R^6$ is halogen; and a salt selected from the group consisting of iodonium salts, thiapyrylium salts, diazonium salts and ferrocenium salts, said salt being a salt of a non-nucleophilic anion.

2. The composition of claim 1, wherein the onium salt is an iodonium salt.

3. The composition of claim 2 wherein the iodonium salt is a diaryliodonium salt.

4. the composition of claim 3 wherein the iodonium salt is selected from the group consisting of diaryliodonium hexaflurophosphates, diaryliodonium arsenates, diaryliodonium antimonates and diaryliodonium hexafluoroborates.

5. The composition of claim 4 wherein the iodonium salt is (4-octyloxyphenyl) phenyliodonium hexafluoroantimonate or 4,4'-dimethytdiphenyliodonium tetrafluoroborate.

6. The composition of claim 1 wherein said composition further contains an N,N dialkylaniline selected from the group consisting of 2,6-diethyl-N,N dimethylaniline, N,N, 2,4,6-pentamethylaniline (PMA), p-t-butyl-N,N-dimethylaniline, and N,N-dimethyl-2,6-diisopropylaniline.

7. The composition of claim 1 wherein said polymerizable compound is an epoxy compound or a vinyl ether.

8. The composition of claim 1 wherein said dye is represented by the Formula (I).

9. The composition of claim 8 wherein said dye is represented by the Formula (III) or (IV)

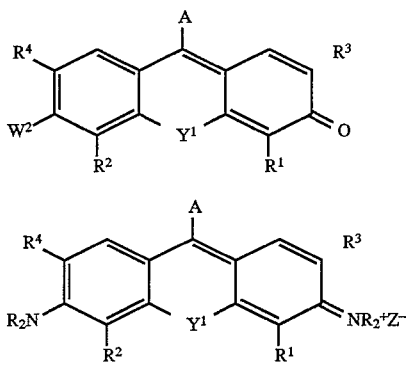

where A is hydrogen, aryl, alkyl, alkenyl, alkynyl, dicholorotriazinylamino, or an electron withdrawing group (EWG) selected from group consisting of $COOR^{11}$, $COR^{12}$, $C(O)OCOR^{11}$, $CONR_2$, $CN$, $NO_2$, $NCS$, $NCO$, $SO_2R^{11}$, $SO_2NR_2$, and $CX_3$ where $R^{11}$ is hydrogen alkyl aryl or aralkyl, $R^{12}$ is hydrogen, alkyl, aryl, or aralkyl and X can be the same or different and is a halogen; $Y^1$ is oxygen, sulfur or $>NR^{13}$ where $R^{13}$ is 4-methylphenyl; R and $R^1$-$R^4$ are defined as in claim 1; $Z^-$ is a counter ion and $W^2$ is hydrogen or $-OR^9$ and $R^9$ is defined as in claim 1.

10. The composition of claim 9 wherein $Y^1$ is O.

11. The composition of claim 10 wherein said dye is represented by the Formula (III).

12. The composition of claim 11 wherein at least two of $R^1$-$R^4$ are iodo or bromo.

13. The composition of claim 12 wherein A is hydrogen.

14. The composition of claim 15 wherein A is CN.

15. The composition of claim 12 wherein at least two of $R^1$-$R^4$ are iodo.

16. The composition of claim 9 wherein $W^2$ is $-OR^9$ and $R^9$ is hydrogen or a $C_1$-$C_8$ alkyl group.

17. The composition of claim 11 wherein said dye is selected from the group consisting of:

5,7-diiodo-3-methoxy-6-fluorone (DIMF),
5,7-diiodo-3-ethoxy-6-fluorone (DIEF),
5,7-diiodo-3-butoxy-6-fluorone (DIBF),
5,7-diiodo-3-octoxy-6-fluorone (DIOF),
4,5-diiodo-3-hydroxy-6-fluorone,
9-cyano-5,7-diiodo-3-methoxy-6-fluorone (CDIMF),
9-cyano-5,7-diiodo-3-ethoxy-6-fluorone (CDIEF),
9-cyano-5,7-diiodo-3-butoxy-6-fluorone (CDIBF),
9-cyano-5,7-diiodo-3-octoxy-6-fluorone (CDIOF),
3-hydroxy-2,4,5,7-tetraiodo-6-fluorone (TIHF),
3-hydroxy-2,4,5,7-tetrabromo-6-fluorone (TBHF),
3-hydroxy-2,4,5,7-tetrachloro-6-fluorone (TCHF),
3-hydroxy-2,4,5,7-tetrafluoro-6-fluorone (TFHF),
9-cyano-3-hydroxy-2,4,5,7-tetraiodo-6-fluorone (TIHCF).

18. The composition of claim 12 wherein said dye is represented by formula (III):

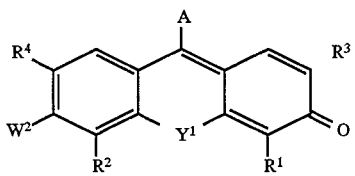

where A is hydrogen or CN; $W^2$ is hydrogen $OR^9$ where $R^9$ is hydrogen or $C_1$-$C_8$ alkyl; $Y^1$ is O; and $R^1$, $R^2$, $R^3$ and $R^4$ are defined as in claim 12.

19. The composition of claim 9 wherein said composition further contains an N,N-dialkylaniline selected from the group consisting of 2,6-diethyl-N,N-dimethylaniline, N,N-2,4,6-pentamethylaniline (PMA), p-t-butyl-N-N-dimethylaniline, and N,N-dimethyl-2,6-diisopropylaniline.

20. A photohardenable composition consisting essentially of a cationically polymerizable compound selected from the group consisting of epoxy compounds, vinyl ethers, vinyl ether functional prepolymers, cyclic ethers, cylic esters, cylic sulfides, melamine-formaldehyde, phenol-formaldehyde, cylic organosiloxanes, lactams, lactones, cylic acetals, and epoxy functional silicone oligomers; a dye represented by the Formula (I) or (II):

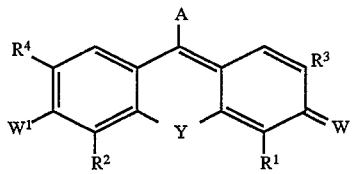

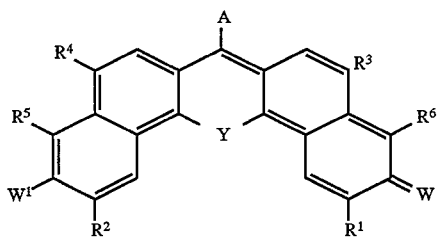

where $R^1$, $R^2$, $R^5$ and $R^6$ are the same or different and represent a hydrogen atom or a halogen atom and where $R^1$ and $R^2$ may combine to form a ring; $R^3$ and $R^4$ are the same or different and represent a hydrogen atom, a halogen atom, a benzoyl group, a group of the formula $-L(CH_2)_nR^8$ where n is 1 to 8, $R^8$ is hydrogen, hydroxy, amino, dialkylamino, $-COR^{16}$ or $-COOR^{14}$ where $R^{16}$ is hydrogen, chlorine, COC1, $C_1$-$C_8$ alkyl, $NR_2$, or aryl, and $R^{14}$ is hydrogen, $C_1$-$C_8$ alkyl, aryl, COR, $NR_2$; and L is a direct bond or $>C=O$; W is O $>NR_2^+$, $W^1$ is hydrogen or $-OR^9$ where $R^9$ is hydrogen, $C_1$-$C_8$ alkyl, acyl or a group of the formula $-(CH_2)_nR^{10}$ where n is 1 to 8 and $R^{10}$ is amino, dialkylamino, hydroxy, acryloyl or methacryioyl and when W is $NR_2^+$, $W^1$ is hydrogen or $-NR_2$; Y is oxygen, sulfur, selenium, tellurium, $>C=O$, or $>NR^{13}$ where $R^{13}$ is 4-methylphenyl, A is hydrogen, aryl, alkenyl, alkyl, alkynyl, dichlorotriazinylamino or an electron withdrawing group (EWG) which is selected from the group consisting of $COOR^{11}$, $COR^{12}$, $C(O)OCOR^{11}$, $CONR_2$, $CN$, $NO_2$, $NCS$, $NCO$, $SO_2R^{12}$, $SO_3R^{11}$, $SO_2NR_2$, and $CX_3$ where $R^{11}$ is a hydrogen, alkyl, aryl or aralkyl; and X can be the same or different and is a halogen; provided that at least one $R^1$-$R^6$ is halogen; a hydrogen donor and a salt selected from the group consisting of iodonium salts, thiapyrylium salts, diazonium salts and ferrocenium salts, said salt being a salt of a non-nucleophilic anion.

21. The composition of claim 20 wherein said dye is represented by the Formula (III) or IV:

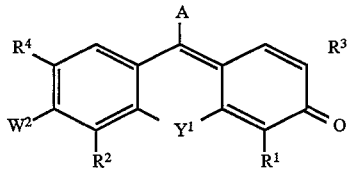

-continued

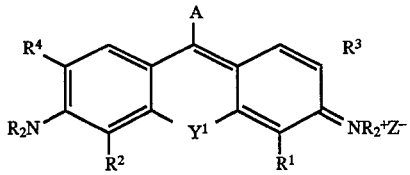

IV where A is hydrogen, aryl, alkyl, alkenyl, alkynyl, dichlorotriazinylamino or an electron withdrawing group selected from the group consisting of $COOR^{11}$, $COR^{12}$, $C(O)OCOR^{11}$, $CONR_2$, $CN$, $NO_2$, $NCS$, $NCO$, $SO_2R^{11}$, $SO_2NR$, and $CX_3$ where $R^{11}$ is hydrogen, alkyl, aryl, or aralkyl, $R^{12}$ is hydrogen, alkyl, aryl, or aralkyl and X can be the same or different and is a halogen; $Y^1$ is oxygen, sulfur or $>RN^{13}$ where $R^{13}$ is 4-methylphenyl; R and $R^1$-$R^4$ are defined as in claim 20; $Z^-$ is a counter ion and $W^2$ is hydrogen or $-OR^9$ and $R^9$ is defined in claim 20.

22. The composition of claim 20, wherein the salt is an iodonium salt.

23. The composition of claim 22, wherein the iodonium salt is a diaryliodonium salt.

24. The composition of claim 23, wherein the iodonium salt is selected from the group consisting of diaryliodonium hexafluorophosphates, diaryliodonium arsenates, diaryliodonium antimonates, and diaryliodonium tetrafluoroborates.

25. The composition of claim 24, wherein the iodonium salt is (4-octyloxy-phenyl) phenyliodonium hexaflurooarsenate or 4,4'-dimethyl diphenyliodonium tetrafluoroborate.

26. A photohardenable composition which comprises a cationically polymerizable compound selected from the group consisting of epoxy compounds and, vinyl ethers; a dye selected from the group consisting of 5,7-diiodo-3-methoxy-6-fluorone (DIMF), 5,7-diiodo-3-ethoxy-6-fluorone (DIEF), 5,7-diiodo-3-butoxy-6-fluorone (DIBF), 5,7-diiodo-3-octoxy-6-fluorone (DIOF), 4,5-diiodo-3-hydroxy-6-fluorone, 9-cyano- 5,7-diiodo-3-methoxy-6-fluorone (CDIMF), 9-cyano- 5,7-diiodo-3-ethoxy-6-fluorone (CDIEF), 9-cyano- 5,7-diiodo-3-butoxy-6-fluorone (CDIBF), 9-cyano- 5,7-diiodo-3-octoxy-6-fluorone (CDIOF), 3-hydroxy-2,4,5,7-tetraiodo-6-fluorone (TIHF), 3-hydroxy-2,4,5,7-tetrabromo-6-fluorone (TBHF), 3-hydroxy-2,4,5,7-tetrachloro-6-fluorone (TCHF), 3-hydroxy-2,4,5,7-tetrafluoro-6-fluorone (TFHF), 9-cyano-3-hydroxy-2,4,5,7-tetraiodo-6-fluorone (TIHCF); and an iodonium salt selected from the group consisting of diaryliodonium hexafluorophosphates, diaryliodonium arsenates, and diaryliodonium antimonates.

* * * * *

UNITED STATES PATENT AND TRADEMARK OFFICE
CERTIFICATE OF CORRECTION

PATENT NO.   : 5,639,802
DATED        : June 17, 1997
INVENTOR(S)  : Neckers et al.

It is certified that error appears in the above-indentified patent and that said Letters Patent is hereby corrected as shown below:

Claim 1, Col. 18, line 28, the term --, chlorine -- should be inserted after "hydrogen".

Claim 4, Col. 18, line 49, at the beginning of the claims, "the" should be -- The --.

Claim 4, Col. 18, line 52, "hexafluoroborates" should be -- tetrafluoroborates --.

Claim 5, Col. 18, line 56, "4,4' dimethytdi-phenyliodonium" should be -- 4,4' dimethyldiphenyliodonium --.

Claim 9, Col. 19, line 20, "hydrogen alkyl" should be -- hydrogen, alkyl, --.

Claim 9, Col. 19, line 22, the term -- atom -- should be inserted after "halogen".

Claim 14, Col. 19, line 32, "15" should be -- 12 --.

Claim 18, Col. 19, line 55, "12" should be -- 9 --.

Claim 18, Col. 19, line 67, "12" should be -- 9 --.

Claim 20, Col. 20, line 9, "cylic" should be -- cyclic --.

UNITED STATES PATENT AND TRADEMARK OFFICE
CERTIFICATE OF CORRECTION

PATENT NO. : 5,639,802
DATED : June 17, 1997
INVENTOR(S) : Neckers et al.

It is certified that error appears in the above-indentified patent and that said Letters Patent is hereby corrected as shown below:

Claim 20, Col. 20, line 10, "cylic" should be -- cyclic --.

Claim 20, Col. 20, line 11, "cylic" should be -- cyclic --.

Claim 20, Col. 20, line 12, "cylic" should be -- cyclic --.

Claim 20, Col. 20, line 41, "O>NR$_2^+$" should be -- O or NR$_2^+$ --.

Claim 20, Col. 20, line 43, "methacryioyl" should be -- methacryloyl --.

Signed and Sealed this

Twenty-seventh Day of July, 1999

Attest:

Q. TODD DICKINSON

*Attesting Officer*    *Acting Commissioner of Patents and Trademarks*